United States Patent [19]
Belletire et al.

[11] 4,442,114
[45] Apr. 10, 1984

[54] IMIDE DERIVATIVES

[75] Inventors: John L. Belletire, Madison, Wis.; Reinhard Sarges, Mystic, Conn.

[73] Assignee: Pfizer Inc., New York, N.Y.

[21] Appl. No.: 458,700

[22] Filed: Jan. 17, 1983

Related U.S. Application Data

[62] Division of Ser. No. 292,751, Aug. 13, 1981, abandoned, which is a division of Ser. No. 106,577, Dec. 26, 1979, Pat. No. 4,307,108.

[51] Int. Cl.$^3$ ............... C07D 211/88; A61K 31/445
[52] U.S. Cl. .................................. 424/267; 424/274; 546/17; 548/411
[58] Field of Search ............... 548/411; 546/17; 424/274, 267

[56] References Cited

U.S. PATENT DOCUMENTS

| | | | |
|---|---|---|---|
| 3,507,881 | 4/1970 | Sandberg | 260/326.5 |
| 3,539,575 | 11/1970 | Skorcz | 546/17 |
| 3,647,797 | 3/1972 | Carr et al. | 546/17 |
| 3,821,383 | 6/1974 | Sestanj et al. | 424/258 |
| 4,307,108 | 12/1981 | Belletire et al. | 548/411 |

OTHER PUBLICATIONS

Brittain et al.; Chem. Abs., vol. 98:143291e, (1983).
J. Faust et al., in the *Journal of the American Pharmaceutical Association*, vol. XLVI, No. 2, p. 118, (1957).

*Primary Examiner*—Mary C. Lee
*Attorney, Agent, or Firm*—Charles J. Knuth; Peter C. Richardson

[57] ABSTRACT

A series of spiro-imide compounds and their base salts with pharmacologically acceptable cations are disclosed. These particular compounds are useful in therapy as agents for the control of certain chronic diabetic complications. Preferred member compounds include 2,3-dihydro-spiro-[1H-indene-1,3'-pyrrolidone]-2',5'-dione, 2,3-dihydro-spiro-[1H-indene-2,3'-pyrrolidine]-2',5'-dione, 3,4-dihydro-spiro-[2H-naphthalene-1,3'-pyrrolidine]-2',5'-dione, 3,4-dihydro-spiro-[2H-naphthalene-1,3'-piperidine]-2',6'-dione, 6-chloro-2,3-dihydro-spiro-[4H-1-benzopyran-4,3'-pyrrolidine]-2',5'-dione and 6,7-dihydro-spiro-[5H-benzo(b)thiophene-4,3'-pyrrolidine]-2',5'-dione. Methods for preparing these compounds from known starting materials are provided.

2 Claims, No Drawings

IMIDE DERIVATIVES

This is a division of application Ser. No. 292,751, filed on Aug. 13, 1981, abandoned, which is, in turn, a division of application Ser. No. 106,577, filed Dec. 26, 1979 and now U.S. Pat. No. 4,307,108.

BACKGROUND OF THE INVENTION

This invention relates to new and useful imide derivatives of principal interest to those in the field of medicinal chemistry and/or chemotherapy. More particularly, it is concerned with a novel series of spiro-imide compounds, which are of especial value in view of their ability to effectively control certain chronic complications arising from diabetes mellitus (e.g., diabetic cataracts, retinopathy and neuropathy). The invention also includes a new method of therapy within its scope.

In the past, various attempts have been made by numerous investigators in the field of organic medicinal chemistry to obtain new and better oral antidiabetic agents. For the most part, these efforts have involved the testing of various organic compounds in an endeavor to determine their ability to lower blood sugar (i.e., glucose) levels. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 do disclose that certain aldose reductase inhibitors like 1,3-diazo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of various diabetic subjects are thereby prevented or reduced. As a result, these compounds control certain chronic diabetic complications, including those of an ocular nature, since it is already known in the art that the presence of polyols in the lens of the eye quite often leads to cataract formation and concomitant loss of lens clarity.

SUMMARY OF THE INVENTION

In accordance with the present invention, it has now been rather surprisingly found that various spiroimide compounds are extremely useful when employed in therapy as agents for the control of certain chronic complications arising in a diabetic subject even though they are not outstanding aldose reductase inhibitors per se. More specifically, the novel method of treatment of the present invention involves treating a diabetic host to prevent or alleviate diabetes-associated chronic ocular and neuritic complications by administering to said host an effective amount of a compound of the formulae:

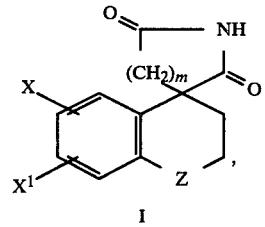

I

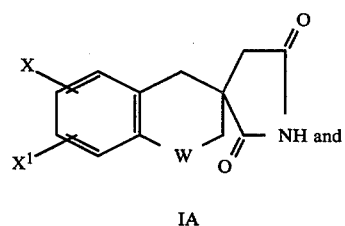

IA

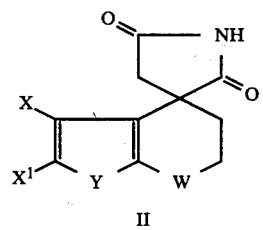

II and the base salts thereof with pharmacologically acceptable cations, wherein W is $-(CH_2)_n-$; X is hydrogen, chlorine, lower alkyl or lower alkoxy; $X^1$ is hydrogen, fluorine, chlorine, bromine, lower alkyl, lower alkoxy or phenyl, with the proviso that when $X^1$ is fluorine, bromine or phenyl, X is hydrogen; Y is oxygen or sulfur; Z is W, Y or Q wherein Q is oxosulfur or dioxosulfur; m is one or two; and n is zero or one. These compounds possess the ability to markedly reduce or even inhibit sorbitol accumulation in the less and peripheral nerves of various diabetic subjects.

The compounds of this invention which are novel are those of formula I wherein Z is Y or Q as previously defined or Z is $(CH_2)_n$ and n is zero. Additionally, those compounds of formula II per se are also all novel compounds. Accordingly, the novel compounds of this invention comprise spiro-imides of the formulae:

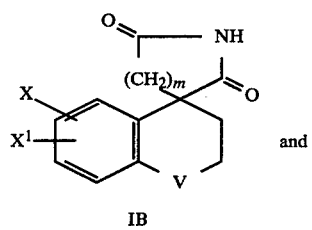

IB and

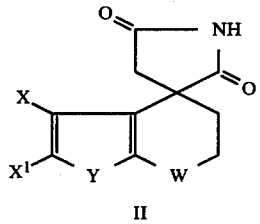

II and the base salts thereof with pharmacologically acceptable cations, wherein W is —(CH$_2$)$_n$—; X is hydrogen, chlorine, lower alkyl or lower alkoxy; X$^1$ is hydrogen, fluorine, chlorine, bromine, lower alkyl, lower alkoxy or phenyl, with the proviso that when X$^1$ is fluorine, bromine or phenyl, X is hydrogen; Y is oxygen or sulfur; V is oxygen, sulfur, oxosulfur or dioxosulfur; m is one or two; and n is zero or one.

Of especial interest in this connection are such typical and preferred member compounds of the invention as 2,3-dihydro-spiro-[1H-indene-1,3'-pyrrolidine]-2',5'-dione, 2,3-dihydro-spiro-[1H-indene-2,3'-pyrrolidine]-2',5'-dione, 3,4-dihydro-spiro-[2H-naphthalene-1,3'-pyrrolidine]-2',5'-dione, 3,4-dihydro-spiro-[2H-naphthalene-1,3'-piperidine]-2',6'-dione, 6-chloro-2,3-dihydro-spiro-[4H-1-benzopyran-4,3'-pyrrolidone]-2',5'-dione and 6,7-dihydro-spiro-[5H-benzo(b)thiophene-4,3'-pyrrolidine]-2',5'-diene, respectively. These key compounds are all particularly effective in lowering sorbitol levels in the sciatic nerve and lens of diabetic subjects as well as galactitol levels in the lens of galactosemic subjects for the present purposes at hand. The preferred compounds are, as previously indicated, all new compounds with the sole exception of 3,4-dihydro-spiro-[2H-naphthalene-1,3'-pyrrolidine]-2',5'-dione which, although a known compound, was not previously recognized to be of value for the herein disclosed use.

DETAILED DESCRIPTION OF THE INVENTION

In accordance with the process employed for preparing the compounds of this invention of formula I when m is one and of formulae IA-II as previously defined, an appropriately substituted carbonyl ring compound, such as the corresponding 1-indanone, 2-indanone, 1-tetralone, 4-chromanone, thiochroman-4-one, 6,7-dihydrobenzo(b)furan-4(5H)-one and 6,7-dihydrobenzo(b)thiophene-4(5H)-one, of the respective formulae:

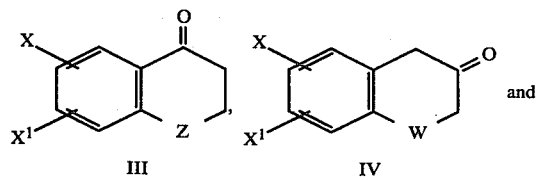

III IV

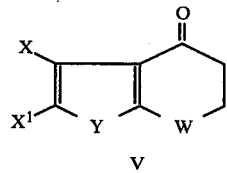

V wherein W, X, X$^1$, Y and Z are all as previously defined, is condensed with a lower alkyl α-cyanoacetate to give the corresponding cyano-iylidene acetate such as, for example, α-cyano-α-(2,3-dihydro-1H-indene-1-ylidene)acetic acid, which is then treated with potassium cyanide to form the corresponding dicyano compound followed by acid hydrolysis in a conventional manner to yield the corresponding dicarboxylic acid and finally, heat treatment of the latter compound with ammonium hydroxide to ultimately yield the desired spiro-imide final product of the structural formulae previously indicated. In practice, the last step of the process is usually conducted by heating the reaction mixture in an oil bath at high temperatures and preferably at a temperature that is in the range of from about 200° C. up to about 300° C., i.e., until at least all the volatile material is removed from the mixture and the resultant product forms a homogeneous mass. In this way, 1-indanone is converted via α-cyano-α-(2,3-dihydro-1H-indene-1-ylidene)acetic acid ethyl ester and α-cyano-α-(2,3-dihydro-1H-indene-1-yl)butanedioic acid, respectively, to 2,3-dihydro-spiro-[1H-indene-1,3'-pyrrolidene]-2',5'-dione per se.

On the other hand, compounds of the invention of formula I where m is two are best prepared by a series of reactions starting from the corresponding α-cyano ring compound of the formula:

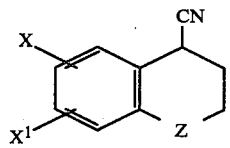

wherein X, X$^1$ and Z are each as previously defined, which series of reactions involves treating said starting material with 3-bromopropanenitrile in the presence of a basic condensing agent like sodium hydride to form the corresponding dinitrile, followed by alkaline hydrolysis of the latter compound to yield the monoamide of the corresponding dicarboxylic acid and finally, heat treatment of the latter acid-amide with ammonium hydroxide in the same manner as that described previously for the last step of the first process to ultimately yield the desired spiro-imide of structural formula I wherein m is two. In this way, α-cyanotetralin is converted via α-(3,4-dihydro-2H-naphthalene-1-yl)-n-pentane-1,5-dinitrile and α-(3,4-dihydro-2H-naphthalene-1-yl)-n-pentane-1,5-dioic acid monoamide, respectively, to 3,4-dihydro-spiro-[2H-naphthalene-1,3'-piperidine]-2',6'-dione per se.

Compounds of the invention in which Z of formula I is Q and Q is

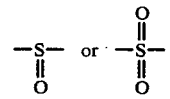

can be prepared from those compounds wherein Z is sulfur by merely oxidizing the latter group of compounds in accordance with standard techniques well known to those skilled in the art. For instance, the use of sodium periodate in this connection leads to the formation of the oxosulfur compounds, while peroxy acids like peracetic acid, perbenzoic acid and m-chloroperoxybenzoic acid, etc., are preferably employed to afford the corresponding dioxosulfur compounds. On the other hand, certain compounds of the invention having a ring substituent (X, X$^1$, etc.) which is halogen (as previously defined) may alternatively be prepared from the corresponding unsubstituted compounds wherein at least one of X and X$^1$ is hydrogen by means of direct halogenation techniques well known to those in the field of synthetic organic chemistry.

The ketone starting materials (i.e., carbonyl ring compounds) required for preparing the spiro-imide intermediates of this invention are, for the most part, known compounds and are either readily available commercially, like 1-indanone, 2-indanone, 6-chloro-4-chromanone and 6,7-dihydrobenzo(b)thiophene-4(5H)-one, etc., or else they can easily be synthesized by those skilled in the art starting from common chemical reagents and using conventional methods of organic synthesis. For instance, 6-fluoro-4-chromanone is obtained by condensing β-(p-fluorophenoxy)propionic acid in the presence of polyphosphoric acid, while 6,7-dichlorothiochroman-4-one is obtained by condensing β-(3,4-dichlorophenylthio)propionic acid in the presence of concentrated sulfuric acid. In both cases, the starting organic acid is ultimately derived from a commercially available compound.

The chemical bases which are used as reagents in this invention to prepare the aforementioned pharmaceutically acceptable base salts are those which form non-toxic salts with the herein described acidic spiro-imides such as 2,3-dihydro-spiro-[1H-indene-1,3′-pyrrolidine]-2′,5′-dione, for example. These particular non-toxic base salts are of such a nature that their cations are essentially non-toxic in character over the wide range of dosage administered. Examples of such cations include those of sodium, potassium, calcium and magnesium, etc. These salts can easily be prepared by simply treating the aforementioned spiro-imide compounds with an aqueous solution of the desired pharmacologically acceptable base, such as the hydroxide, carbonate or bicarbonate of one of the aforementioned cations, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution to dryness in the same manner as before. In either case, stoichiometric quantities of reagents should be employed in order to ensure completeness of reaction and maximum yields of the desired final product.

As previously indicated, the spiro-imide compounds of this invention reduce lens sorbitol levels in diabetic subjects. For instance, 2,3-dihydro-spiro-[1H-indene-1,3′-pyrrolidine]-2′,5′-dione, a typical and preferred agent of the present invention, has been found to inhibit the formation of sorbitol levels in the sciatic nerve of diabetic rats to a significant degree when given by the oral route of administration at a dose level as low as 2.5 mg./kg. without showing any substantial signs of toxic side effects. The other compounds of this invention also cause similar results. Furthermore, the herein described compounds can be administered by either the oral or parenteral routes of administration without causing any significant untoward pharmacological side reactions in the subjects to whom they are so administered. These compounds are ordinarily administered in dosages ranging from about 0.25 mg. to about 25 mg. per kg. of body weight per day, although variations will necessarily occur depending upon the actual condition of the subject being treated and the particular route of administration chosen.

The spiro-imide compounds of this invention may be administered either alone or in combination with pharmaceutically acceptable carriers, and such administration can be carried out in both single and multiple dosages. The compounds of this invention can be administered in a wide variety of dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. The oral pharmaceutical formulations can be suitably sweetened and/or flavored by means of various agents of the type commonly employed for such purposes. In general, the compounds of the invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various combinations thereof.

For parenteral administration, solutions of these spiro-imides in sesame or peanut oil or in aqueous propylene glycol or N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. The sterile aqueous media employed are all readily obtainable by standard techniques well-known to those skilled in the art. Additionally, it is also possible to administer the aforesaid spiro-imide compounds topically via an appropriate ophthalmic solution which can then be applied dropwise to the eye.

The activity of the compounds of the present invention, as agents for the control of chronic diabetic complications, is determined by their ability to successfully pass one or more of the following standard biological and/or pharmacological tests, viz., (1) measuring their ability to reduce or inhibit sorbitol accumulation in the sciatic nerve of acutely streptozotocinized (i.e., diabetic) rats; (2) measuring their ability to reverse already-elevated sorbitol levels in the sciatic nerve and lens of chronic streptozotocin-induced diabetic rats; (3) measuring their ability to prevent or inhibit galactitol formation in the lens of acutely galactosemic rats, and (4) measuring their ability to delay cataract formation and reduce the severity of lens opacities in chronic galactosemic rats.

PREPARATION A

6-Fluoro-4-chromanone was prepared according to the procedure described by R. Sarges in U.S. Pat. No. 4,117,230, starting from β-(p-fluorophenoxy)propionic acid [Finger et al., *Journal of the American Chemical Society*, Vol. 81, p.94 (1959)] and using polyphosphoric acid as the condensing agent. The product obtained was identical in every respect with the prior art compound.

PREPARATION B 6,7-Dichlorothiochroman-4-one was prepared according to the procedure described by R. Sarges in U.S. Pat. No. 4,117,230, starting from 3,4-dichlorobenzenethiol (available from the Aldrich Chemical Company, Inc., Milwaukee, Wis.) and proceeding thru β-(3,4-dichlorophenylthio)propionic acid, which was then condensed in the presence of concentrated sulfuric acid to afford the desired product. The latter material was identical in every respect with the prior art compound.

PREPARATION C

The procedure described by J. A. Faust et al., in the *Journal of the American Pharmaceutical Association*, Vol. XLVI, No. 2, p.118 (1957), for the preparation of 1,2,3,4-tetrahydro-spiro-[naphthalene-2,3'-pyrrolidine]-2',5'-dione, starting from 2-carboxy-1,2,3,4-tetrahydronaphthaleneacetic acid and using 28% aqueous ammonia as the reagent, was followed here except that 1-carboxy-1,2,3,4-tetrahydro-1-naphthaleneacetic acid was the actual starting material employed in place of the corresponding 2-positional isomer. In this particular case, the corresponding final product obtained was 3,4-dihydro-spiro-[2H-naphthalene-1,3'-pyrrolidine]-2',5'-dione, m.p. 153°–156° C. (literature m.p. 155°–157° C., according to R. V. Sandberg in U.S. Pat. No. 3,507,881).

Anal. Calcd. for $C_{13}H_{13}NO_2$: C, 72.54; H, 6.09; N, 6.51. Found: C, 72.19; H, 6.17; N, 6.30.

EXAMPLE 1

A mixture consisting of 10 g. (0.0758 mole) of 1-indanone (available from the Aldrich Chemical Company, Inc., Milwaukee, Wis.), 12 ml. (12.6 g., 0.1115 mole) of ethyl cyanoacetate, 3 ml. of glacial acetic acid and 3 g. of ammonium acetate in 100 ml. of benzene was heated under reflux in a suitable reaction flask equipped with a Dean-Stark trap (water separator) for a period of 18 hours. An additional 2 g. of ammonium acetate were then added, followed by further refluxing for a period of 24 hours. At the end of this time, the spent reaction mixture was cooled to room temperature (~25° C.), diluted with benzene and then washed with water. The separated organic layer was subsequently dried over anhydrous magnesium sulfate and filtered, followed by removal of the solvent via evaporation under reduced pressure. In this manner, there was obtained a crystalline residue which was later recrystallized from ethyl acetate to yield 12 g. (70%) of pure α-cyano-α-(2,3-dihydro-1H-indene-1-ylidene)acetic acid ethyl ester, m.p. 98°–101° C.

To a stirred solution consisting of 3.0 g. (0.0132 mole) of the 1-indenylidene compound obtained above dissolved in 20 ml. of ethanol at room temperature (~25° C.), there were added 2.5 g. (0.0385 mole) of potassium cyanide dissolved in 20 ml. of water. The resulting mixture was then refluxed for a period of 20 minutes and at the end of this time, it was cooled and subsequently acidified with concentrated hydrochloric acid. The spent reaction mixture was then extracted three times with benzene and the benzene layers were saved, and subsequently combined and evaporated to near dryness while under reduced pressure to afford a highly viscous residue. The latter residue was then dissolved in 15 ml. of glacial acetic acid, and the resulting solution subsequently treated with 28 ml. of 12 N hydrochloric acid and refluxed for a period of 48 hours. At the end of this time, the strongly acid solution was cooled to room temperature and concentrated in vacuo to afford a residue that later was triturated with water. The precipitated solids so obtained were then recovered by means of suction filtration and thereafter recrystallized from ethanol to give 1.26 g. (43%) of pure (2,3-dihydro-1H-indene-1-yl)butanedioic acid, m.p. 185°–187° C.

Anal. Calcd. for $C_{12}H_{12}O_4$: C, 65.44; H, 5.49. Found: C, 65.39; H, 5.53.

A mixture consisting of 3.0 g (0.0136 mole) of the above diacid and 3.5 ml. of concentrated ammonium hydroxide was heated in an oil bath maintained at 260° C., allowing the liquid to be removed from the mixture by means of distillation under reduced pressure (a pressure of 60 mm. Hg was actually employed). The residue so obtained was then triturated with isopropanol, and the resulting precipitated solids were subsequently recovered by means of suction filtration and thereafter recrystallized from ethyl acetate to yield 1.3 g. (48%) of pure 2,3-dihydro-spiro-[1H-indene-1,3'-pyrrolidine]-2',5'-dione, m.p. 148°–150° C.

Anal. Calcd. for $C_{12}H_{11}NO_2$: C, 71.72. H, 5.51; N, 6.96. Found: C, 71.31; H, 5.56; N, 6.93.

EXAMPLE 2

A mixture consisting of 3.0 g. (0.017 mole) of 6-chloro-4-chromanone (available from the Aldrich Chemical Company, Inc., Milwaukee, Wis.), 15 ml. (15.75 g., 0.1394 mole) of ethyl cyanoacetate and 10 g. of ammonium acetate in 300 ml. of benzene was heated according to the procedure described in Example 1 (where the corresponding 1-indanone compound was the starting material employed) to give 1.3 g. (29%) of crude ethyl α-cyano-α-(6-chloro-2,3-dihydro-4H-1-benzopyran-4-ylidene)acetic acid ethyl ester, which was used in the next reaction step without any further purification being necessary.

To a stirred solution consisting of the above benzopyranylidene compound (1.3 g., 0.00493 mole) in 9.5 ml. of ethanol, there were added 1.13 g. of potassium cyanide in 9.5 ml. of water and the resulting mixture was refluxed according to the procedure described in Example 1 (where the corresponding 1-indenylidene compound was the starting material employed) and worked up in essentially the same manner as before (except that the residue was dissolved in 6 ml. of glacial acetic acid and treated with 12.7 ml. of concentrated hydrochloric acid prior to refluxing for the last time). In this manner, there was ultimately obtained 0.39 g. (29%) of crude α-(6-chloro-2,3-dihydro-4H-1-benzopyran-4-yl)butanedioc acid, m.p. 189°–190.5° C. after further recrystallization from ethanol.

A mixture consisting of 237 mg. (0.00088 mole) of the above diacid and 4.5 ml. of concentrated ammonium hydroxide was then heated in the same manner as described in Example 1 for the corresponding 1-carboxy-1-indanacetic acid and isolated in the same manner as before to give pure 6-chloro-2,3-dihydro-spiro-[4H-1-benzopyran-4,3'-pyrrolidine]-2',5'-dione, m.p. 225°–226° C. after recrystallization from ethyl acetate/ethanol/n-hexane.

Anal. Calcd. for $C_{12}H_{10}ClNO_3$: C, 57.27; H, 4.00; N, 5.57. Found: C, 57.25; H, 4.00; N, 5.54.

EXAMPLE 3

A mixture consisting of 10 g. (0.0758 mole) of 2-indanone (available from the Aldrich Chemical Company, Inc., Milwaukee, Wis.), 8.6 g. (0.0761 mole) of ethyl cyanoacetate, 1 ml. of piperidine and 1 ml. of glacial acetic acid in 65 ml. of benzene was heated under reflux in suitable reaction flask equipped with a Dean-Stark trap for a period of 18 hours. Upon completion of this step, the reaction mixture was cooled to room temperature (~25° C.) and poured into 250 ml. of water, followed by separation of the resulting organic layers and then drying of same over anhydrous magnesium sulfate. After removal of the drying agent by means of filtration and the solvent by means of evaporation under reduced pressure, there was obtained a crystalline residue, which was subsequently recrystallized from n-hexane to yield 6.5 g. (38%) of pure α-cyano-α-(2,3-dihydro-1H-indene-2-ylidene)acetic acid ethyl ester, m.p. 112°–114° C. [literature m.p. 116° C., according to the *Journal of the Chemical Society*, Vol. 115, p. 150 (1919)].

Anal. Calcd. for $C_{14}H_{13}NO_2$: C, 73.99; H, 5.76; N, 6.17. Found: C, 74.10; H, 5.84; N, 6.22.

To a stirred solution consisting of 6.5 g. (0.0286 mole) of the 2-indenylidene compound obtained above dissolved in 35 ml. of ethanol at room temperature, there were added 3.8 g. (0.0385 mole) of potassium cyanide dissolved in 35 ml. of water and the resulting mixture was refluxed for a period of 15 minutes according to the procedure described in Example 1 (where the corresponding 1-indanone compound was the starting material employed) and worked up in essentially the same manner as before (except that ethyl acetate rather than benzene was the solvent employed in the extraction step, and the residue was dissolved in 25 ml. of glacial acetic acid and treated with 50 ml. of concentrated hydrochloric acid prior to refluxing for the last time). However, in this particular case, the final residue obtained was diluted with 50 ml. of water and then extracted three times with ethyl acetate, followed by a re-extraction of the combined organic layers (three times) with dilute aqueous sodium bicarbonate solution. On acidification of the combined aqueous layers with 6 N hydrochloric acid, there was finally obtained a fine crystalline precipitate, which was subsequently collected by means of suction filtration and air dried to constant weight to yield 4.5 g. of crude product. Recrystallization of the latter material from ethyl acetate/n-hexane then gave 3.1 g. (49%) of pure α-(2,3-dihydro-1H-indene-2-yl)butanedioic acid, m.p. 166°–168° C.

A mixture consisting of 1.5 g. (0.0068 mole) of the above diacid and 2.0 ml. of concentrated ammonium hydroxide was heated gradually to 300° C. (bath temperature) according to the same general procedure described in Example 1 for the preparation of the corresponding 1-isomer. The residue so obtained was then cooled to room temperature and dissolved in 200 ml. of isopropanol, followed by treatment with charcoal and filtration in the usual manner. The clear alcoholic filtrate which resulted was then concentrated in vacuo to ca. 75 ml. and the desired product was allowed to crystallize slowly therefrom while at room temperature. The precipitated solids (480 mg.) were subsequently collected by means of suction filtration and thereafter recrystallized from isopropanol to give 260 mg. (19%) of pure 2,3-dihydro-spiro-[1H-indene-2,3'-pyrrolidine]-2',5'-dione, m.p. 173°–175° C.

Anal. Calcd. for $C_{12}H_{11}NO_2$: C, 71.62; H, 5.51; N, 6.96. Found: C, 71.65; H, 5.58; N, 6.91.

EXAMPLE 4

A mixture consisting of 10 g. (0.0657 mole) of 6,7-dihydrobenzo(b)thiophene-4(5H)-one (available from the Aldrich Chemical Company, Inc., Milwaukee, Wis.), 7.5 g. (0.0664 mole) of ethyl cyanoacetate, 1 ml. of piperidine and 1 ml. of glacial acetic acid in 65 ml. of benzene was heated according to the general procedure described in Example 1 (where the corresponding 1-indanone compound was the starting material employed) to ultimately give (after distillation of the oily residue) 4.5 g. (28%) of pure α-cyano-α-[6,7-dihydro-5H-benzo(b)thiophene-4-ylidene]acetic acid ethyl ester, b.p. 156°–160° C./0.3 mm Hg.

To a stirred solution consisting of 4.5 g. (0.0182 mole) of the 4-thiopheneylidene compound obtained above dissolved in 20 ml. of ethanol, there were added 2.34 g. (0.036 mole) of potassium cyanide dissolved in 20 ml. of water and the resulting mixture was refluxed according to the procedure described in Example 1 (where the corresponding 1-indenylidene compound was the starting material employed) and work-up in essentially the same manner as before. In this manner, there were ultimately obtained 2.83 g. (65%) of pure α-[6,7-dihydro-5H-benzo(b)thiophene-4-yl]butanedioc acid, m.p. 164°–167° C.

A mixture consisting of 1.4 g. (0.00583 mole) of the above diacid and 2.0 ml. of concentrated ammonium hydroxide was then heated in the same manner as described in Example 1 for the corresponding 1-carboxy-1-indanacetic acid and isolated in the same manner as before to ultimately yield 290 mg. (23%) of pure 6,7-dihydro-spiro-[5H-benzo(b)thiophene-4,3'-pyrrolidine]-2',5'-dione m.p. 188°–190° C. after recrystallization from isopropanol/diethyl ether.

Anal. Calcd. for $C_{11}H_{11}NO_2S$: C, 59.70; H, 5.01; N, 6.33. Found: C, 59.87; H, 5.17; N, 6.48.

EXAMPLE 5

A solution consisting of 760 mg. (0.0048 mole) of α-cyanotetralin [*Chemical Abstracts*, Vol. 47, p. 80576 (1953)] dissolved in 15 ml. of dry dimethylformamide was heated to 45° C. in a three-necked roundbottomed reaction flask, while under a dry nitrogen atmosphere, with 228 mg. (0.0050 mole) of 56% sodium hydride (in mineral oil) for a period of 45 minutes. At the end of this time, 0.6 ml. (969 mg., 0.00723 mole) of 3-bromopropanenitrile was added to the mixture and the latter mixture was then stirred at room temperature (~25° C.) overnight for a period of approximately 10 hours. The resulting reaction mixture was then diluted with water, followed by the addition of 600 ml. of ethyl acetate to the cooled aqueous mixture. The separated organic layer was then washed with water and dried over anhydrous magnesium sulfate. After removal of the drying agent by means of filtration and the solvent by means of evaporation under reduced pressure, there was obtained 1.1 g. of crude α-(3,4-dihydro-2H-naphthalene-1-yl)-n-pentane-1,5-dinitrile in the form of an oil as residue.

A mixture consisting of 2.2 g. (0.0105 mole) of the above crude dinitrile in 25 ml. of ethanol and 23 ml. of 4 N aqueous potassium hydroxide was heated under reflux for a period of two days. At the end of this time, the reaction mixture was cooled to room temperature (~25° C.) and diluted with 50 ml of water and 300 ml. of methylene chloride, followed by treatment with 3 N hydrochloric until acidification was achieved. The resulting organic layer was then collected and subsequently extracted three times with 4 N aqueous potassium hydroxide solution, followed by acidification of the combined aqueous layers and their subsequent extraction with fresh methylene chloride. Upon removal of the latter solvent from the final (i.e., separated) organic layer by means of evaporation under reduced pressure, there was obtained a crystalline residue which was subsequently recrystallized from ethylene chloride/n-hexane/diethyl ether to give 628 mg. (24%) of pure α-(3,4-dihydro-2H-naphthalene-1-yl)-n-pentane-1,5-dioic acid monoamide, m.p. 143°–145° C.

Anal. Calcd. for $C_{14}H_{17}NO_3$: C, 67.99; H, 6.93; N, 5.66. Found: C, 67.50; H, 6.68; N, 5.47.

A mixture consisting of 600 mg. (0.00243 mole) of the above acid-amide and 20 ml. of concentrated ammonium hydroxide was heated according to the same general procedure described in Example 1 for a period of three hours to ultimately give (after isolation in the usual manner as before) 343 mg. (62%) of pure 3,4-dihydrospiro-[2H-naphthalene-1,3'-piperidine]-2',6'-dione, m.p. 173°–175° C. after recrystallization from ethanol/n-hexane.

Anal. Calcd. for $C_{14}H_{15}NO_2$: C, 73.34; H, 6.59; N, 6.11. Found: C, 73.24; H, 6.47; N, 6.09.

EXAMPLE 6

The following spiro-imide compounds may be prepared by employing the procedures described in the previous examples, starting from readily available materials in each instance:

6-methoxy-2,3-dihydro-spiro-[1H-indene-1,3'-pyrrolidine]-2',5'-dione.

6-fluoro-2,3-dihydro-spiro-[1H-indene-1,3'-pyrrolidine]-2',5'-dione.

5,6-dimethoxy-2,3-dihydro-spiro-[1H-indene-1,3'-pyrrolidine]-2',5'-dione.

5-methoxy-2,3-dihydro-spiro-[1H-indene-2,3'-pyrrolidine]-2',5'-dione.

6-chloro-2,3-dihydro-spiro-[1H-indene-1,3'-piperidine]-2',5'-dione.

6-bromo-2,3-dihydro-spiro-[1H-indene-2,3'-pyrrolidine]-2',5'-dione.

5-methyl-2,3-dihydro-spiro-[1H-indene-1,3'-piperidine]-2',5'-dione.

6-(n-butyl)-spiro-[1H-indene-2,3'-pyrrolidine]-2',5'-dione.

5-phenyl-spiro-[1H-indene-1,3'-pyrrolidine]-2',5'-dione.

5,6-dichloro-spiro-[1H-indene-1,3'-pyrrolidine]-2',5'-dione.

5,6-dimethyl-spiro-[1H-indene-2,3'-pyrrolidine]-2',5'-dione.

-methoxy-3,4-dihydro-spiro-[2H-naphthalene-1,3'-pyrrolidine]-2',5'-dione.

6,7-dimethoxy-3,4-dihydro-spiro-[2H-naphthalene-1,3'-pyrrolidine]-2',5'-dione.

6-methoxy-3,4-dihydro-spiro-[2H-naphthalene-1,3'-piperidine]-2',5'-dione.

5-methoxy-3,4-dihydro-spiro-[2H-naphthalene-2,3'-pyrrolidine]-2',5'-dione.

7-fluoro-3,4-dihydro-spiro-[2H-naphthalene-1,3'-pyrrolidine]-2',5'-dione.

7-chloro-3,4-dihydro-spiro-[2H-naphthalene-1,3'-piperidine]-2',5'-dione.

6-bromo-3,4-dihydro-spiro-[2H-naphthalene-2,3'-pyrrolidine]-2',5'-dione.

6-methyl-3,4-dihydro-spiro-[2H-naphthalene-1,3'-pyrrolidine]-2',5'-dione.

7-(n-butoxy)-3,4-dihydro-spiro-[2H-naphthalene-1,3'-pyrrolidine]-2',5'-dione.

6-phenyl-3,4-dihydro-spiro-[2H-naphthalene-1,3'-pyrrolidine]-2',5-dione 6,7-dichloro-3,4-dihydro-spiro-[2H-naphthalene-1,3'-pyrrolidine]-2',5'-dione.

6,7-diethyl-3,4-dihydro-spiro-[2H-naphthalene-1,3'-piperidine]-2',5'-dione.

6,7-dimethoxy-3,4-dihydro-spiro-[2H-naphthalene-2,3'-pyrrolidine]-2',5'-dione. 6-methoxy-2,3-dihydrospiro-[4H-1-benzopyran-4,3'-pyrrolidine]-2',5'-dione.

6-methoxy-2,3-dihydro-spiro-[4H-1-benzopyran-4,3'-pyrrolidine]-2',5'-dione.

6-fluoro-2,3-dihydro-spiro-[4H-1-benzopyran-4,3'-pyrrolidine]-2',5'-dione.

6,7-dichloro-2,3-dihydro-spiro-[4H-1-benzopyran-4,3'-pyrrolidine]-2',5'-dione.

6,8-dichloro-2,3-dihydro-spiro-[4H-1-benzopyran-4,3'-piperidine]-2',5'-dione.

8-chloro-2,3-dihydro-spiro-[4H-1-benzopyran-4,3'-pyrrolidine]-2',5'-dione.

6-bromo-2,3-dihydro-spiro-[4H-1-benzopyran-4,3'-piperidine]-2',5-dione.

6,8-dimethyl-2,3-dihydro-spiro-[4H-1-benzopyran-4,3'-pyrrolidine]-2',5'-dione.

6-(n-butyl)-2,3-dihydro-spiro-[4H-1-benzopyran-4,3'-pyrrolidine]-2',5'-dione.

7-methyl-2,3-dihydro-spiro-[4H-1-benzopyran-4,3'-piperidine]-2',5'-dione.

6-(n-butoxy)-2,3-dihydro-spiro-[4H-1-benzopyran-4,3'-pyrrolidine]-2',5'-dione.

6,7-dimethoxy-2,3-dihydro-spiro-[4H-1-benzopyran-4,3'-pyrrolidine]-2',5'-dione.

7-phenyl-2,3-dihydro-spiro-[4H-1-benzopyran-4,3'-pyrrolidine]-2',5'-dione.

2,3-dihydro-spiro-[4H-1-benzothiapyran-4,3'-pyrrolidine]-2',5'-dione.

6-methoxy-2,3-dihydro-spiro-[4H-1-benzothiapyran-4,3'-pyrrolidine]-2',5'-dione.

6-chloro-2,3-dihydro-spiro-[4H-1-benzothiapyran-4,3'-pyrrolidine]-2',5'-dione.

6-bromo-2,3-dihydro-spiro-[4H-1-benzothiapyran-4,3'-piperidine]-2',5'-dione.

6,7-dichloro-2,3-dihydro-spiro-[4H-1-benzothiapyran-4,3'-pyrrolidine]-2',5'-dione.

6-fluoro-2,3-dihydro-spiro-[4H-1-benzothiapyran-4,3'-pyrrolidine]-2',5'-dione.

8-chloro-2,3-dihydro-spiro-[4H-1-benzothiapyran-4,3'-pyrrolidine]-2',5'-dione.

7-chloro-2,3-dihydro-spiro-[4H-1-benzothiapyran-4,3'-piperidine]-2',5'-dione.

6-methyl-2,3-dihydro-spiro-[4H-1-benzothiapyran-4,3'-pyrrolidine]-2',5'-dione.

7-(n-butyl)-2,3-dihydro-spiro-[4H-1-benzothiapyran-4,3'-pyrrolidine]-2',5'-dione.

7-(n-butoxy)-2,3-dihydro-spiro-[4H-1-benzothiapyran-4,3'-pyrrolidine]-2',5'-dione.

6-phenyl-2,3-dihydro-spiro-[4H-1-benzothiapyran-4,3'-pyrrolidine]-2',5'-dione.

6,8-dichloro-2,3-dihydro-spiro-[4H-1-benzothiapyran-4,3'-piperidine]-2',5'-dione.

6,7-dimethyl-2,3-dihydro-spiro-[4H-1-benzothiapyran-4,3'-pyrrolidine]-2',5'-dione.

6,7-dimethoxy-2,3-dihydro-spiro-[4H-1-benzothiapyran-4,3'-pyrrolidine]-2',5'-dione.

2,3-dihydro-spiro-[4H-1-benzothiapyran-4,3'-pyrrolidine]-2',5'-dione-1-oxide.
6-fluoro-2,3-dihydro-spiro-[4H-1-benzothiapyran-4,3'-pyrrolidine]-2',5'-dione-1-oxide.
8-chloro-2,3-dihydro-spiro-[4-H-1-benzothiapyran-4,3'-pyrrolidine]-2',5'-dione-1-oxide.
6-bromo-2,3-dihydro-spiro-[4H-1-benzothiapyran-4,3'-piperidine]-2',5'-dione-1-oxide.
6-methyl-2,3-dihydro-spiro-[4H-1-benzothiapyran-4,3'-pyrrolidine]-2',5'-dione-1-oxide.
6-methoxy-2,3-dihydro-spiro-[4H-1-benzothiapyran-4,3'-pyrrolidine]-2',5'-dione-1-oxide.
6-phenyl-2,3-dihydro-spiro-[4H-1-benzothiapyran-4,3'-pyrrolidine]-2',5'-dione-1-oxide.
6,8-dichloro-2,3-dihydro-spiro-[1H-1-benzothiapyran-4,3'-piperidine]-2',5'-dione-1-oxide.
6,7-dimethyl-2,3-dihydro-spiro-[4H-1-benzothiapyran-4,3'-pyrrolidine]-2',5'-dione-1-oxide.
6,7-dimethoxy-2,3-dihydro-spiro-[4H-1-benzothiapyran-4,3'pyrrolidine]-2',5'-dione-1-oxide.
2,3-dihydro-spiro-[4H-1-benzothiapyran-4,3'-pyrrolidine]-2',5'-dione-1,1-dioxide.
6-fluoro-2,3-dihydro-spiro-[4H-1-benzothiapyran-4,3'-pyrrolidine]-2',5'-dione-1,1-dioxide.
8-chloro-2,3-dihydro-spiro-[4H-1-benzothiapyran-4,3'-pyrrolidine]-2',5'-dione-1,1-dioxide.
6-methyl-2,3-dihydro-spiro-[4H-1-benzothiapyran-4,3'-pyrrolidine]-2',5'-dione-1,1-dioxide.
6-methoxy-2,3-dihydro-spiro-[4H-1-benzothiapyran-4,3'-pyrrolidine]-2',5'-dione-1,1-dioxide.
6-phenyl-2,3-dihydro-spiro-[4H-1-benzothiapyran-4,3'-pyrrolidine]-2',5'-dione-1,1-dioxide.
6,8-dichloro-2,3-dihydro-spiro-[4H-1-benzothiapyran-4,3'-piperidine]-2',5'-dione-1,1-dioxide.
6,7-dimethyl-2,3-dihydro-spiro-[4H-1-benzothiapyran-4,3'-pyrrolidine]-2',5'-dione-1,1-dioxide.
6,7-dimethoxy-2,3-dihydro-spiro-[4H-1-benzothiapyran-4,3'-pyrrolidine]-2',5'-dione-1,1-dioxide.
2-chloro-6,7-dihydro-spiro-[5H-benzo(b)thiophene-4,3'-pyrrolidine]-2',5'-dione.
2-bromo-6,7-dihydro-spiro-[5H-benzo(b)thiophene-4,3'-pyrrolidine]-2',5'-dione.
2-methyl-6,7-dihydro-spiro-[5H-benzo(b)thiophene-4,3'-pyrrolidine]-2',5'-dione.
2-methoxy-6,7-dihydro-spiro-[5H-benzo(b)thiophene-4,3'-pyrrolidine]-2',5'-dione.
2-phenyl-6,7-dihydro-spiro-[5H-benzo(b)thiophene-4,3'-pyrrolidine]-2',5'-dione.
2,3-dichloro-6,7-dihydro-spiro-[5H-benzo(b)thiophene-4,3'-pyrrolidine]-2',5'-dione.
2,3-dimethyl-6,7-dihydro-spiro-[5H-benzo(b)thiophene-4,3'-pyrrolidine]-2',5'-dione.
2,3-dimethoxy-6,7-dihydro-spiro-[5H-benzo(b)thiophene-4,3'-pyrrolidine]-2',5'-dione.
spiro-[cyclopenta(b)thiophene-4,3'-pyrrolidine]-2',5'-dione.
2-chloro-spiro-[cyclopenta(b)thiophene-4,3'-pyrrolidine]-2',5'-dione.
2-(n-propyl)-spiro-[cyclopenta(b)thiophene-4,3'-pyrrolidine]-2',5'-dione.
2-ethoxy-spiro-[cyclopenta(b)thiophene-4,3'-pyrrolidine]-2',5'-dione.
2-phenyl-spiro-[cyclopenta(b)thiophene-4,3'-pyrrolidine]-2',5'-dione.
2,3-dichloro-spiro-[cyclopenta(b)thiophene-4,3'-pyrrolidine]-2',5'-dione.
2,3-dimethyl-spiro-[cyclopenta(b)thiophene-4,3'-pyrrolidine]-2',5'-dione.
6,7-dihydro-spiro-[5H-benzo(b)furan-4,3'-pyrrolidine]-2',5'-dione.
2-chloro-6,7-dihydro-spiro-[5H-benzo(b)furan-4,3'-pyrrolidine]-2',5'-dione.
2-methyl-6,7-dihydro-spiro-[5H-benzo(b)furan-4,3-pyrrolidine]-2',5'-dione.
2-methoxy-6,7-dihydro-spiro-[5H-benzo(b)furan-4,3'-pyrrolidine]-2',5'-dione.
2-phenyl-6,7-dihydro-spiro-[5H-benzo(b)furan-4,3'-pyrrolidine]-2',5'-dione.
2,3-dichloro-6,7-dihydo-spiro-[5H-benzo(b)furan-4,3'-pyrrolidine]-2',5'-dione.
2,3-dimethyl-6,7-dihydro-spiro-[5H-benzo(b)furan-4,3'-pyrrolidine]-2',5'-dione.
2,3-dimethoxy-6,7-dihydro-spiro-[5H-benzo(b)furan-4,3'-pyrrolidine]-2',5'-dione.
spiro-[cyclopenta(b)furan-4,3'-pyrrolidine]-2',5'-dione.
2-chloro-spiro-[cyclopenta(b)furan-4,3'-pyrrolidine]-2',5'-dione.
2-methyl-spiro-[cyclopenta(b)furan-4,3'-pyrrolidine]-2',5'-dione.
2-methoxy-spiro-[cyclopenta(b)furan-4,3'-pyrrolidine]-2',5'-dione.
2-phenyl-spiro-[cyclopenta(b)furan-4,3'-pyrrolidine]-2',5'-dione.
2,3-dichloro-spiro-[cyclopenta(b)furan-4,3'-pyrrolidine]-2',5'-dione.
2,3-dimethyl-spiro-[cyclopenta(b)furan-4,3'-pyrrolidine]-2',5'-dione.

EXAMPLE 7

The sodium salt of 3,4-dihydro-spiro-[1H-indene-1,3'-pyrrolidine]-2',5'-dione may be prepared by dissolving said compound in water containing an equivalent amount in moles of sodium hydroxide and then freeze-drying the mixture. In this way, the desired alkali metal salt of the imide is obtained in the form of an amorphous powder which is freely-soluble in water.

In like manner, the potassium and lithium salts are also similarly prepared, as are the other alkali metal salts of all of the other spiro-imide compounds of this invention which are reported earlier in Preparation C and Examples 2-6, respectively.

EXAMPLE 8

The calcium salt of 2,3-dihydro-spiro-[1H-indene-1,3'-pyrrolidine]-2',5'-dione may be prepared by dissolving said compound in water containing an equivalent amount in moles of calcium hydroxide and then freeze-drying the mixture. The corresponding magnesium salt is also prepared in like manner, as are all the other alkaline-earth metal salts not only of this particular compound, but also of those spiro-imides previously described in Preparation C and Examples 2-6, respectively.

EXAMPLE 9

A dry solid pharmaceutical composition may be prepared by blending the following materials together in the proportions by weight specified below:

| | |
|---|---|
| 3,4-dihydro-spiro-[1H—indene-1,3'-pyrrolidine]-2',5'-dione | 50 |
| Sodium citrate | 25 |
| Alginic acid | 10 |
| Polyvinylpyrrolidone | 10 |

| -continued | |
|---|---|
| Magnesium stearate | 5 |

After the dried compound is thoroughly blended, tablets are punched from the resulting mixture, each tablet being of such size that it contains 200 mg. of the active ingredient. Other tablets are also prepared in a similar fashion containing 25, 50 and 100 mg. of the active ingredient, respectively, by merely using the appropriate amount of the spiro-imide compound in each case.

EXAMPLE 10

A dry solid pharmaceutical composition may be prepared by combining the following materials together in the proportions by weight indicated below:

| | |
|---|---|
| 2,3-Dihydro-[1H—indene-1,3-pyrrolidine]-2',5'-dione | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE 11

The following spiro-imide compounds of Preparation C and Examples 1–5, respectively, were tested for their ability to reduce or inhibit sorbitol accumulation in the sciatic nerve of streptozotocinized (i.e., diabetic) rats essentially by the procedure described in U.S. Pat. No. 3,821,383. In the present study, the amount of sorbitol accumulation in the sciatic nerves was measured 27 hours after induction of diabetes. The compounds were administered orally at the dose levels indicated 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50–100 mM/g. tissue to as high as 400 mM/g. tissue in the 27-hour test period):

| | Percent Inhibition (%) | | |
|---|---|---|---|
| Compound | 2.5 | 5.0 | 25 mg./kg. |
| Product of Prep. C | — | 46 | — |
| Product of Ex. 1 | 28 | — | — |
| Product of Ex. 2 | — | 13 | — |
| Product of Ex. 3 | — | — | 33 |
| Product of Ex. 4 | — | — | 51 |
| Product of Ex. 5 | — | — | 23 |

We claim:

1. A method of treating a diabetic host to prevent or alleviate diabetes-associated chronic complications, which comprises administering to said host an effective amount of a compound selected from the group consisting of spiro-imides of the formula:

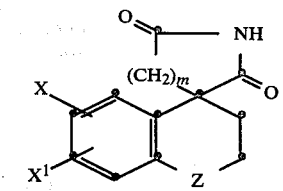

and the base salts thereof with pharmacologically acceptable cations, wherein
W is —(CH$_2$)$_n$—;
X is hydrogen, chlorine, lower alkyl or lower alkoxy;
X$^1$ is hydrogen, fluorine, chlorine, bromine, lower alkyl, lower alkoxy or phenyl, with the proviso that when X$^1$ is fluorine, bromine or phenyl, X is hydrogen;
Y is oxygen or sulfur;
Z is W, Y or Q wherein Q is oxosulfur or dioxosulfur;
m is two; and
n is zero or one.

2. The method as claimed in claim 1 wherein the compound administered is 3,4-dihydro-spiro-[2H-naphthalene-1,3'-piperidine]-2',6'-dione.

* * * * *